United States Patent
Denisenko et al.

(10) Patent No.: US 10,660,820 B2
(45) Date of Patent: May 26, 2020

(54) UNIT FOR ACTION ON BIOLOGICALLY ACTIVE BODY POINTS AND THE RELIEF OF PARAVERTEBRAL MUSCLES

(71) Applicant: YARA LLC, Chelyabinsk (RU)

(72) Inventors: Valeriy Denisenko, Chelyabinsk (RU); Yuriy Koryukalov, Chelyabinsk (RU)

(73) Assignee: Yara LLC, Chelyabinsk (RU)

( * ) Notice: Subject to any disclaimer, the term of this patent is extended or adjusted under 35 U.S.C. 154(b) by 0 days.

(21) Appl. No.: 15/488,266

(22) Filed: Apr. 14, 2017

(65) Prior Publication Data

US 2017/0340514 A1 Nov. 30, 2017

(30) Foreign Application Priority Data

Feb. 15, 2016 (RU) .................................. 2016104968

(51) Int. Cl.
*A61H 39/04* (2006.01)
*A61H 1/02* (2006.01)
(Continued)

(52) U.S. Cl.
CPC .............. *A61H 39/04* (2013.01); *A61F 7/00* (2013.01); *A61H 1/0292* (2013.01); *A61H 1/0296* (2013.01); *A61H 7/001* (2013.01); *A61H 23/00* (2013.01); *A61N 1/0456* (2013.01); *A61N 1/36014* (2013.01); *A61N 2/002* (2013.01); *A61N 5/0619* (2013.01); *A61H 23/02* (2013.01); *A61H 39/08* (2013.01); *A61H 2201/0207* (2013.01); *A61H 2201/10* (2013.01); *A61H 2201/1284* (2013.01); *A61H 2201/1609* (2013.01); *A61H 2201/1623* (2013.01); *A61H 2201/1695* (2013.01); *A61H 2201/50* (2013.01); *A61H 2201/5048* (2013.01); *A61H 2203/0456* (2013.01); *A61H 2205/081* (2013.01)

(58) Field of Classification Search
CPC ............ A61H 39/04; A61H 2201/1695; A61H 1/0292
See application file for complete search history.

(56) References Cited

U.S. PATENT DOCUMENTS

2003/0163176 A1* 8/2003 Bae ......................... A61F 7/007
607/96
2005/0165450 A1* 7/2005 Perez-Torrens ...... A61H 1/0292
606/240
(Continued)

FOREIGN PATENT DOCUMENTS

RU 2465881 4/2011
RU 144668 8/2014

OTHER PUBLICATIONS

English Abstract of RU144668.

Primary Examiner — Carrie R Dorna
(74) Attorney, Agent, or Firm — Preston Smirman; Smirman IP Law, PLLC

(57) ABSTRACT

A unit has been designed to be applied within the area of physiotherapy and is applicable to both medical and athletic therapeutic programs to provide correction of functional states of the spine and the nervous system to eliminate nervous overloads, fatigue, and stress. Moreover, the unit corrects spinal disorders, paravertebral muscular disorders and can be used as a part of mobilizing procedures to act on biologically active body points, and as a part of therapeutic procedures to relieve the spine.

2 Claims, 5 Drawing Sheets

(51) Int. Cl.
*A61F 7/00* (2006.01)
*A61H 7/00* (2006.01)
*A61H 23/00* (2006.01)
*A61N 1/04* (2006.01)
*A61N 1/36* (2006.01)
*A61N 2/00* (2006.01)
*A61N 5/06* (2006.01)
A61H 39/08 (2006.01)
A61H 23/02 (2006.01)

(56) References Cited

U.S. PATENT DOCUMENTS

2006/0142675 A1\* 6/2006 Sargent .................. A61H 39/04
601/70
2009/0259151 A1\* 10/2009 McDonnell ..................... 601/56

\* cited by examiner

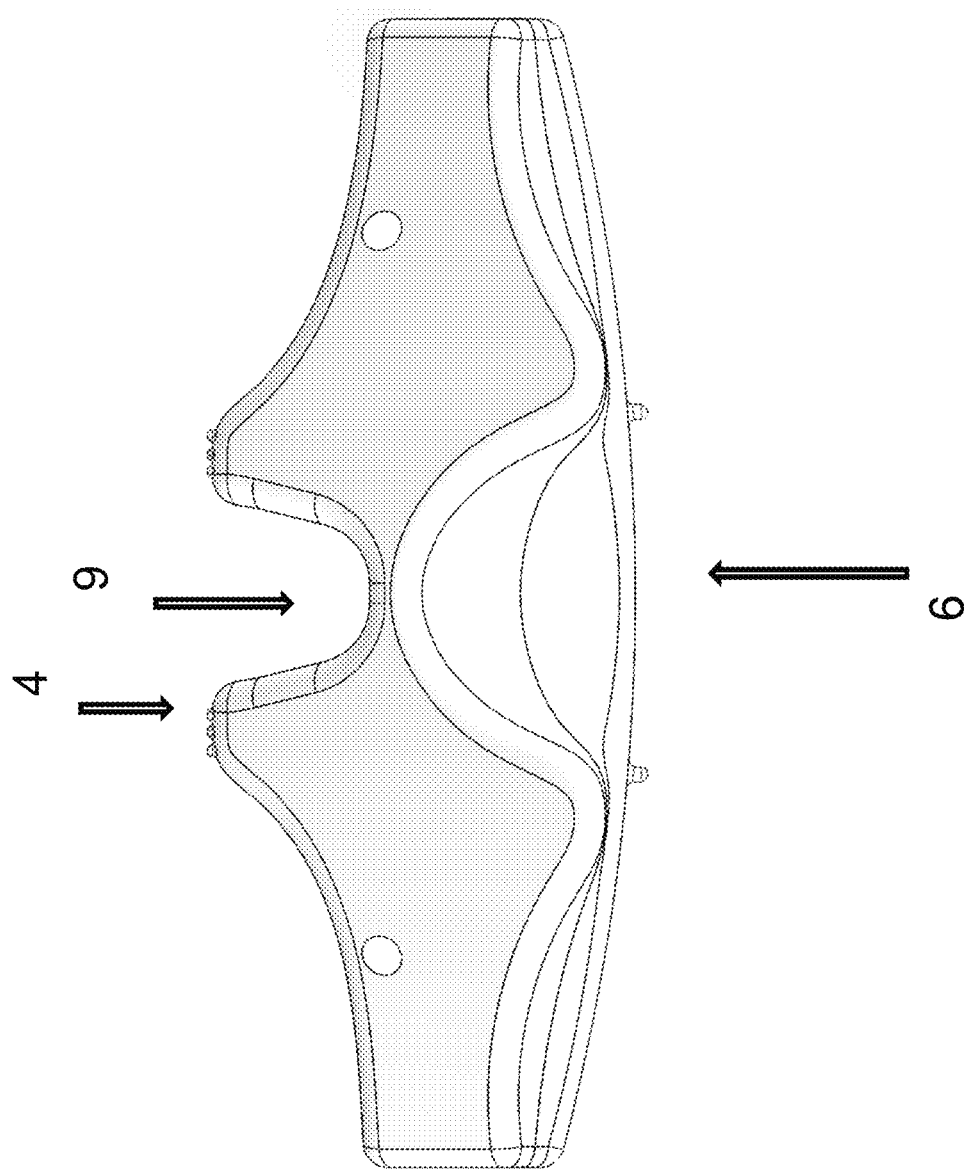

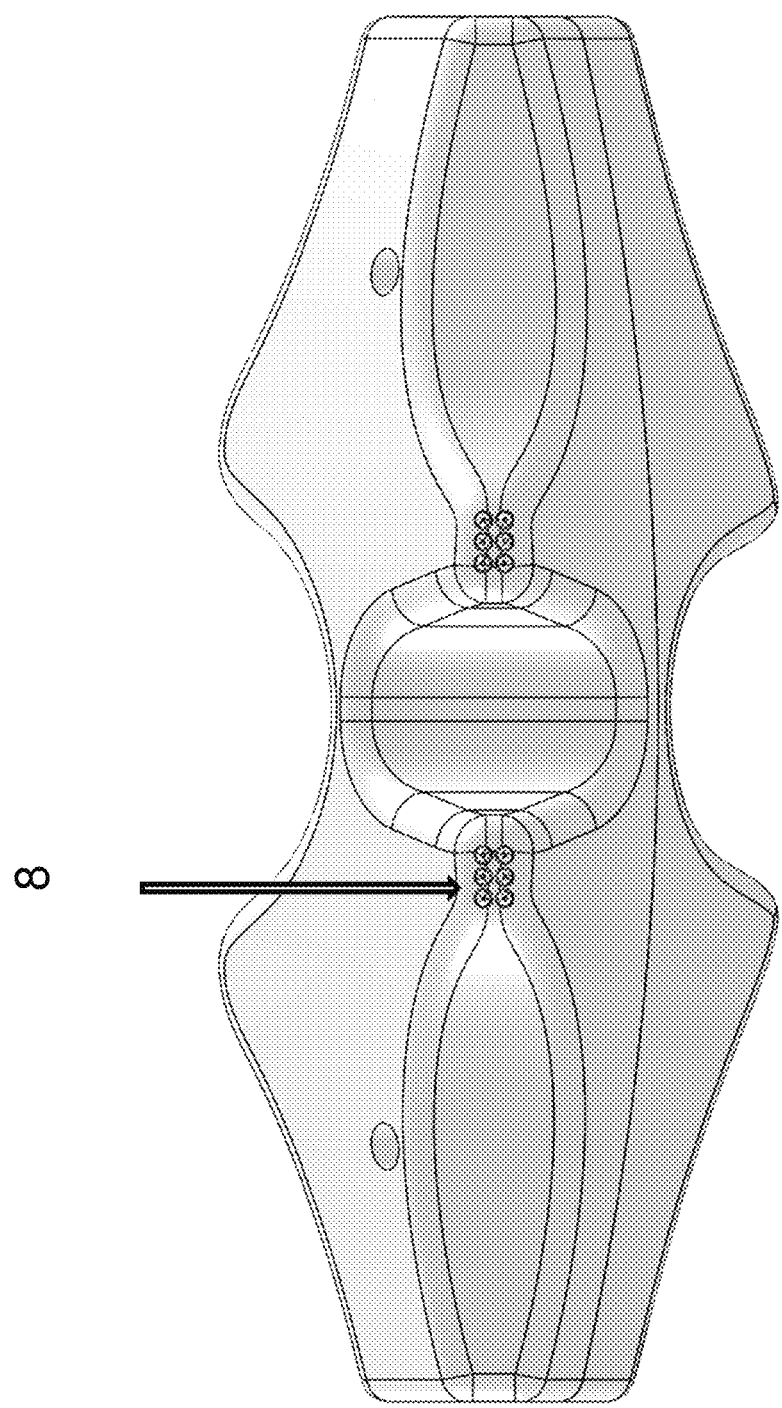

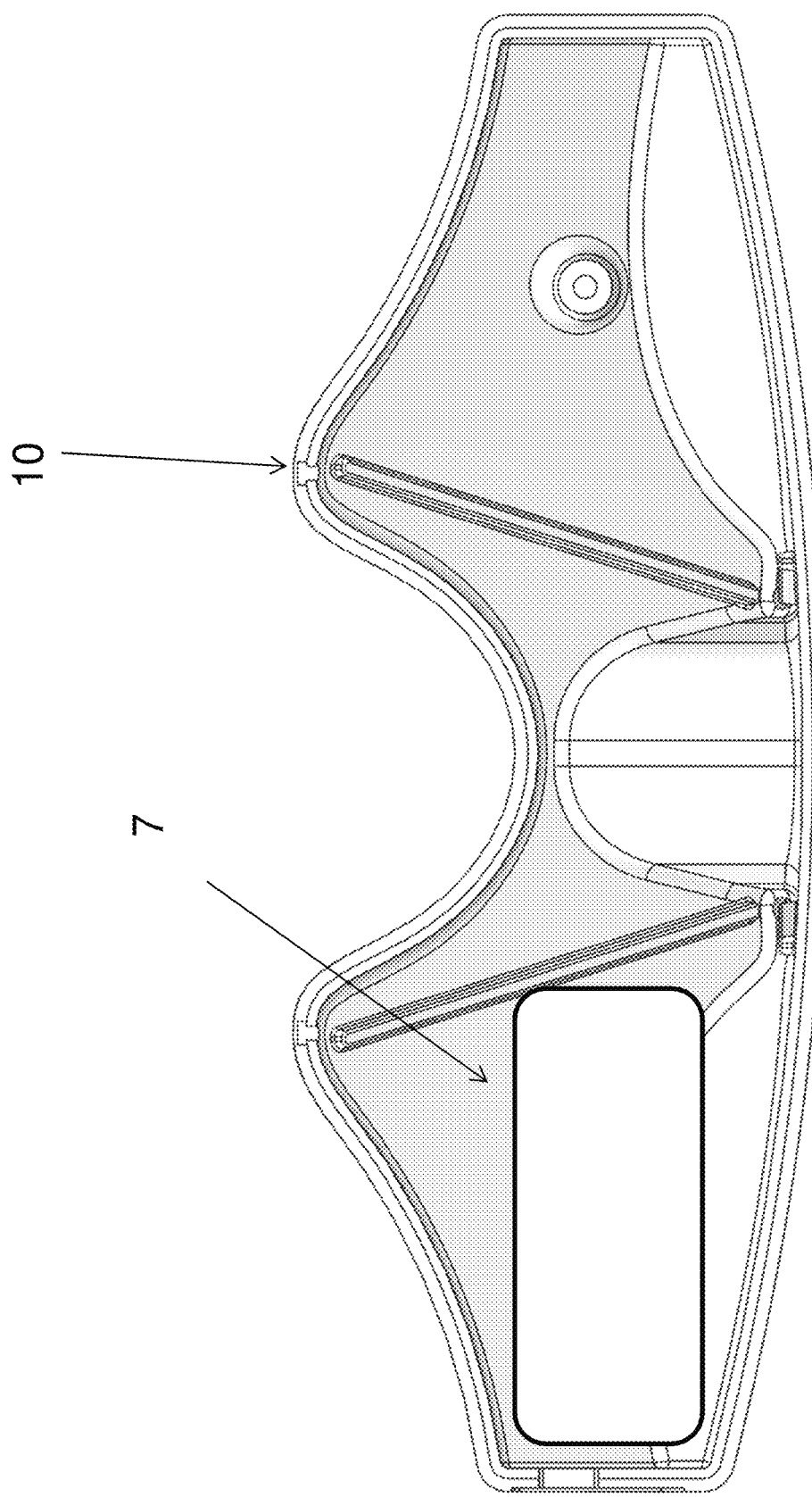

UNIT FOR ACTION ON BIOLOGICALLY ACTIVE BODY POINTS AND THE RELIEF OF PARAVERTEBRAL MUSCLES

CROSS-REFERENCE TO RELATED APPLICATION

The instant application claims priority to Russian Patent Application Serial No. 2016104968 filed Feb. 15, 2016, the entire specification of which is expressly incorporated herein by reference.

FIELD OF THE INVENTION

The unit of the present invention has been designed to be applied within the area of physiotherapy and is applicable to both medical and athletic therapeutic programs to provide correction of functional states of the spine and the nervous system to eliminate nervous overloads, fatigue, and stress. Moreover, the unit corrects spinal disorders, paravertebral muscular disorders, and provides therapeutic relieve of the spine by acting on biologically active body points as a part of therapeutic procedures to relieve the spine.

BACKGROUND OF THE INVENTION

There exist a wide range of efficient therapeutic means and techniques to restore the good functional state of the nervous system, the spine, and the overall human health.

Russian Federation Patent No. 2465881 entitled "The unit for the correction of the spine and paravertebral muscles" and Russian Federation Patent No. 144668 entitled "The unit for the invigoration of the spine and the relief of paravertebral muscles" are the closest analogs to the unit. Each of the analogs in question is fitted with three pairs of massage protrusions to relieve the cervical, the thoracic, and the lumbar regions respectively.

The fact that the massage protrusions of the latter two units are mounted within a narrow rectangular cutout, and, for that reason, often fail to fit to necks of well-built users to provide full immersion of spinous processes into the unit, can be viewed as a substantial design defect.

SUMMARY OF THE INVENTION

It was the principal inventive problem to design a unit for the correction of functional states of the nervous system, for the activation of reflex regulation by acting on bioactive body points, for deep action on muscle-ligamentous apparatus of every individual spinal segment to eliminate spasms in deep-seated paravertebral muscles, and to activate restorative processes and normal mobility of spinal segments in as few sessions as possible, with the corrective effect being good enough for people of any constitution.

Due to the absence of mechanisms for the correction of the nervous system, those previously described conventional units fail to provide complex rehabilitation to spinal problem sufferers, as the spinal problems in question are largely attributed to the state of the nervous system. By comparison, those defects in the latter units prevent action on deep-seated paravertebral neck muscles and sufficient immersion of vertebrae between the protrusions in a safe and efficient way, which results in an incomplete correction of paravertebral areas of the cervical segment and acupuncture action on bioactive body points.

In the light of the above, these have been eliminated by designing a unit for the action on bioactive body points and relief of paravertebral muscles, fitted with two pairs of narrow massage protrusions complete with spikes to correct paravertebral muscles of the thoracic and the lumbar segments, and a pair of wide protrusions for acupuncture action on the cervical region and bioactive body points. The protrusions are generally shaped as pyramids with rounded tops, the spacing being the narrowest between the acupuncture neck massage protrusions and the widest between the lumbar massage protrusions. This unit has pairs of acupuncture protrusions complete with spikes to work on the neck and bioactive body points. The spikes provide deeper targeting of paravertebral muscle fibers of the neck and work on bioactive points and areas of the body.

In marked contrast to the previously described analogs, the unit is fitted with paired electrodes located at the tops of the protrusions to correct the functional state of the nervous system, whether the unit is applied to the spine or other body part. In addition to nervous system correction through the paired electrodes, the unit can exert other types of therapeutic action on paravertebral muscles and bioactive body points.

In accordance with one embodiment of the present invention, a unit for action on biologically active body points and the relief of paravertebral muscles is provided, comprising:

a base member including two pairs of narrow protrusions having spikes for a massage action for correcting a user's paravertebral muscles of the thoracic and the lumbar segments, and a pair of wide protrusions for an acupuncture action on the user's cervical region and bioactive body points;

wherein each of the protrusions are shaped as pyramids with rounded tops, with hollows between each of the protrusions for the user's vertebral spinous processes to fit into;

wherein spacing between each of the protrusion pairs are narrowest between the wide protrusions and are widest between the narrow protrusions;

wherein the pair of wide protrusions is fitted with spikes.

In accordance with one aspect of this embodiment, electrodes at the tops of at least one of the pairs of protrusions are connected with an electronic module of the unit so as to expose the user's skin to therapeutic actions of electric currents, vibrations, magnetic fields, heat, sound, or light.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

Other advantages of the present invention will be readily appreciated as the same becomes better understood by reference to the following detailed description when considered in connection with the accompanying drawings wherein:

FIG. 3 illustrates an acupuncture cervical and lumbar massage protrusions side view;

FIG. 4 illustrates a top view of the acupuncture protrusions complete with cervical spikes; and FIG. 5 illustrates a cross-section of the unit with a schematic representation of the electronic module inside the unit and a layout of the electrodes located at the tops of the protrusions.

The same reference numerals refer to the same parts throughout the various Figures.

DETAILED DESCRIPTION OF THE INVENTION

The following description of the preferred embodiment(s) is merely exemplary in nature and is in no way intended to limit the invention, or uses.

Figure 2:
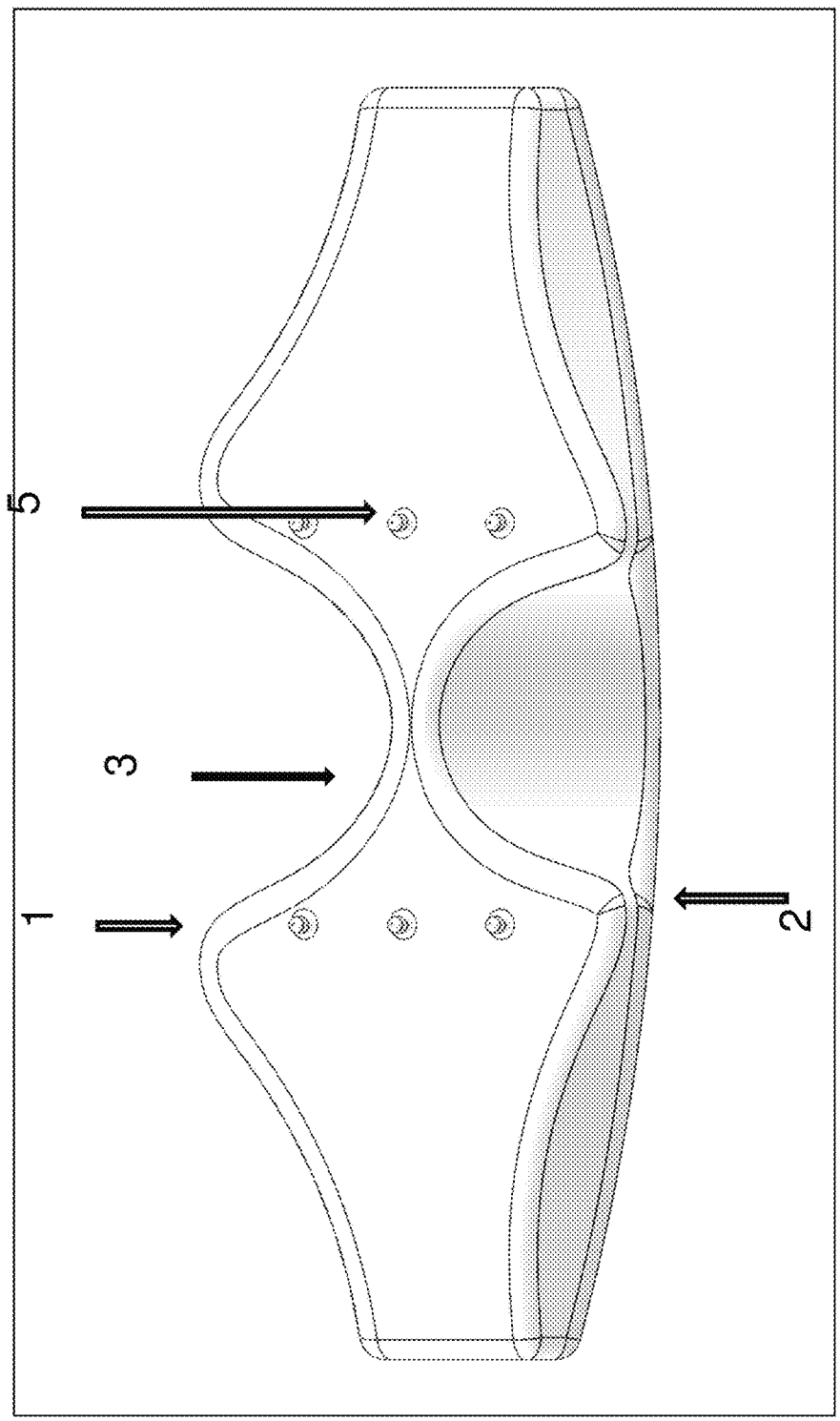
FIG. 2 illustrates a massage thoracic and lumbar massage protrusions side view.

Referring generally to the drawings, the unit for the action on biologically active body points and the paravertebral muscle relief is fitted with two pairs of massage protrusions, 1 and 2, respectively, to relieve the thoracic and the lumbar spinal segments, and a pair of acupuncture protrusions 4 (the spikes of pair 4 are marked with reference element 8) (e.g., see FIGS. 2, 3 and 4).

Figure 1:
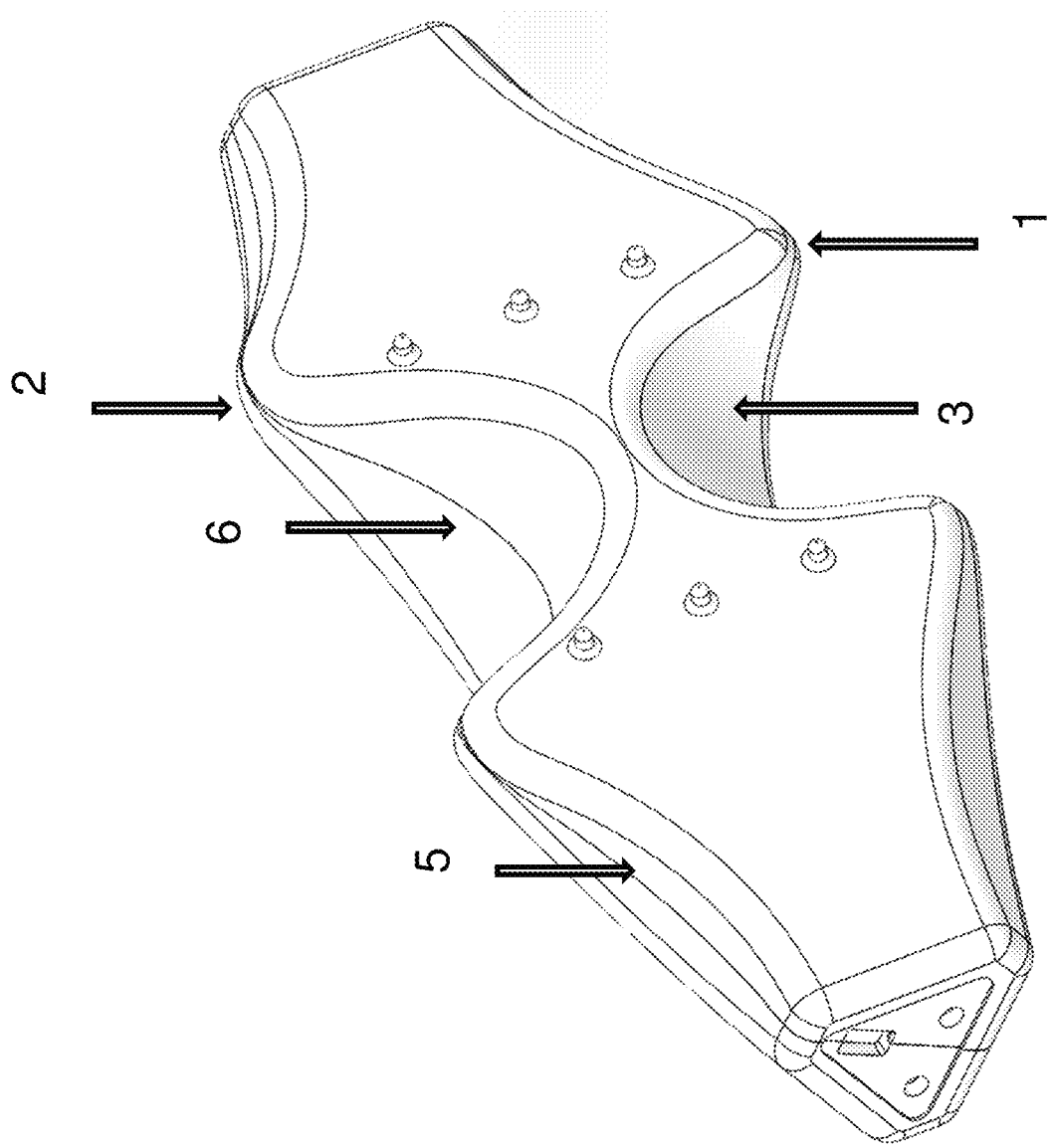
FIG. 1 illustrates a side view of the unit.

The protrusions 1, 2 and 4, respectively, are generally shaped like pyramids with rounded tops with the width of the hollows 3, 6, and 9, respectively, in between generally exceeding 25 mm for vertebral spinous processes to fit into those respective hollows (e.g., see FIGS. 1, 2 and 3). The spans between the protrusions, 1, 2 and 4, respectively, are generally the narrowest between the neck acupuncture protrusions, e.g., 4, and generally the widest between the lumbar massage protrusions, e.g., 1 and/or 2, considering that anatomical widths of respective spinal segments may vary from user to user, depending on their constitutions.

The spikes 5 at the bottom of the unit can keep the unit fixed on any exercise mat when the user is doing relief sessions on any of the spinal segment, in marked contrast to the analogs described in Russian Federation Patent No. 2465881 and Russian Federation Patent No. 144668, respectively, and are prone to slide around the floor.

FIG. 4 shows spikes 8 of the acupuncture protrusions, which provide deeper targeting of paravertebral muscle fibers of the neck and work on bioactive points and areas of the body.

FIG. 5 shows the electronic module inside the unit 7 and the electrodes 10, through which the nervous system receives correction with body currents, while muscles and ligaments receive other correction types, including vibrations, sound, heat, light, and/or magnetic field, which improve restorative processes at the unit application areas.

How to Use the Unit

The user should sit down, and then lay down onto the unit, so that the user's vertebral spinous processes fit into the base of the massage pair 1, 2 or the protrusions 4 of the unit, and remain lying down on the working unit from 2 to 15 minutes, depending on the state of their spine. The session "straightens out" and extends the spine, rendering it to a position contrary to pathological motor stereotypes, relieving the spinal column and restoring balance between antagonist muscles. The acupuncture protrusions 4 can be applied to both the neck and other body parts. The electrodes 10 provide correction of the functional state of the nervous system and facilitate the relief of paravertebral muscles. The protrusions 1, 2 press on the back muscles under the body weight, which relieves muscle hypotonia or hypertonia and activates restorative processes in the muscles, largely due to the programs implemented by means of the electronic module installed inside the unit.

Muscle relaxation, the controlled spine extension pose, the action of the body weight, the acupuncture action of the spines and the versatile action of the unit on spinal segment eliminate pathological blocks from spinal motor segments and restore their normal functional state, while action on bioactive body points activate regulatory processes in the body.

The unit can be used several times a day, doing 10-30 minute-long sessions, depending on the functional state of the user's spine and the overall body health.

The unit improves the efficiency of therapy of spinal and nervous system disorders and dysfunctions by use of body currents and due to the choice of appropriate body positions and poses. It also activates restorative processes, provides instant pain relief, and enhances spinal column amplitudes and speeds up regenerative processes.

The unit is easy to use and takes into account the user's functional state, allowing the user to choose the impact and the session time, with no medical staff involved.

The unit allows to prevent spinal disorders and distress, and to correct postural disorders.

The application areas of the unit include medicinal institutions (including healthcare institutions, preventive medicine institutions, and outpatient care), fitness centers, health centers, athletic facilities, and a domestic environment—as a basis of correctional, therapeutic, and rehabilitative sessions.

While the invention has been described with reference to an exemplary embodiment, it will be understood by those skilled in the art that various changes can be made and equivalents can be substituted for elements thereof without departing from the scope of the invention. In addition, many modifications can be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A unit for action on biologically active body points and the relief of paravertebral muscles of thoracic and lumbar segments, comprising:
    a base member including:
        two pairs of spaced and opposed narrow protrusions formed on a first major face of the base member and having a first set of spikes adapted for a massage action for correcting a user's paravertebral muscles of the thoracic and the lumbar segments, wherein the first set of spikes is adapted to deeply engage fibers of the paravertebral muscles; and
        a pair of wide protrusions formed on a second major face of the base member and adapted for an acupuncture action on the user's cervical region and bioactive body points;
    wherein each of the protrusions are shaped as pyramids with rounded tops, with curved hollows between each of the protrusions adapted for the user's vertebral spinous processes to fit into;
    wherein spacing between each of the protrusion pairs is narrowest between the wide protrusions and is widest between the narrow protrusions;
    wherein the pair of wide protrusions is fitted with a second set of spikes adapted to engage a surface so as to prevent movement of the base member during use by the user.

2. A unit for action on biologically active body points and the relief of paravertebral muscles of thoracic and lumbar segments, comprising:
- a base member including:
    - two pairs of spaced and opposed narrow protrusions formed on a first major face of the base member and having a first set of spikes adapted for a massage action for correcting a user's paravertebral muscles of the thoracic and the lumbar segments, wherein the first set of spikes is adapted to deeply engage fibers of the paravertebral muscles; and
    - a pair of wide protrusions formed on a second major face of the base member and adapted for an acupuncture action on the user's cervical region and bioactive body points;
- wherein each of the protrusions are shaped as pyramids with rounded tops, with curved hollows between each of the protrusions adapted for the user's vertebral spinous processes to fit into; wherein spacing between each of the protrusion pairs is narrowest between the wide protrusions and is widest between the narrow protrusions;
- wherein the pair of wide protrusions is fitted with a second set of spikes adapted to engage a surface so as to prevent movement of the base member during use by the user; and
- electrodes at the tops of at least one of the pairs of protrusions adapted to expose the user's skin to therapeutic actions of electric currents, vibrations, magnetic fields, heat, sound, or light.

* * * * *